United States Patent
St. Amant, III

(10) Patent No.: US 10,215,739 B1
(45) Date of Patent: Feb. 26, 2019

(54) LIQUID BLOCK PROBE FOR WET GAS

(71) Applicant: Mayeaux Holding LLC, Gonzales, LA (US)

(72) Inventor: Valmond Joseph St. Amant, III, St. Amant, LA (US)

(73) Assignee: Mayeaux Holding LLC, Gonzales, LA (US)

(*) Notice: Subject to any disclaimer, the term of this patent is extended or adjusted under 35 U.S.C. 154(b) by 164 days.

(21) Appl. No.: 14/850,815

(22) Filed: Sep. 10, 2015

Related U.S. Application Data

(60) Provisional application No. 62/049,201, filed on Sep. 11, 2014.

(51) Int. Cl.
| | |
|---|---|
| *B01D 50/00* | (2006.01) |
| *G01N 30/32* | (2006.01) |
| *B01D 39/20* | (2006.01) |
| *B01D 53/02* | (2006.01) |
| *G01N 30/02* | (2006.01) |
| *G01N 1/20* | (2006.01) |
| *G01N 1/22* | (2006.01) |
| *G01N 35/00* | (2006.01) |

(52) U.S. Cl.
CPC .......... *G01N 30/32* (2013.01); *B01D 39/2027* (2013.01); *B01D 53/02* (2013.01); *G01N 1/2035* (2013.01); *G01N 1/2205* (2013.01); *G01N 2030/025* (2013.01); *G01N 2030/324* (2013.01); *G01N 2035/00326* (2013.01); *Y10T 137/0396* (2015.04); *Y10T 137/598* (2015.04)

(58) Field of Classification Search
CPC ............. G01N 30/32; G01N 2030/324; G01N 2030/025; G01N 1/2035; G01N 2035/00326; G01N 1/2205; B01D 39/2027; B01D 53/02; Y10T 137/0396; Y10T 137/598

See application file for complete search history.

(56) References Cited

U.S. PATENT DOCUMENTS

| | | | | |
|---|---|---|---|---|
| 2,037,245 A | * | 4/1936 | Leifheit | E21B 43/34 137/193 |
| 2,725,071 A | | 11/1955 | McKillop | |
| 4,348,909 A | * | 9/1982 | Kluth | G01N 1/2035 376/245 |
| 5,579,803 A | | 12/1996 | Welker | |
| 6,041,802 A | * | 3/2000 | Nelson | A47J 37/1271 137/14 |
| 6,357,304 B1 | * | 3/2002 | Mayeaux | G01N 1/2035 73/863.12 |

(Continued)

OTHER PUBLICATIONS

A+ CORP, GENIE 745 Sales Brochure, May 29, 2013, USA.

(Continued)

*Primary Examiner* — Dung H Bui
(74) *Attorney, Agent, or Firm* — Joseph T Regard, Ltd plc

(57) ABSTRACT

A liquid block apparatus integrated into a sample probe that is inserted into the pressurized process to prevent entrained liquids from entering the probe and being extracted for sampling. The present invention enhances sampling of pressurized process fluids for on-stream and spot sampling of pressurized process fluid such as natural gas or the like, particularly pressurized process gas having liquid entrained therein, or otherwise referenced as multiphase or "wet".

41 Claims, 15 Drawing Sheets

(56) References Cited

U.S. PATENT DOCUMENTS

| 7,555,964 | B2 | | 7/2009 | Mayeaux | |
|---|---|---|---|---|---|
| 7,735,513 | B2 | * | 6/2010 | Bush | E03D 5/02 |
| | | | | | 137/489.5 |
| 2002/0036167 | A1 | * | 3/2002 | Mayeaux | G01N 1/2035 |
| | | | | | 210/637 |
| 2015/0168274 | A1 | * | 6/2015 | Sheffield | G01N 1/2205 |
| | | | | | 73/863.12 |

OTHER PUBLICATIONS

McMaster-Carr website image http://wvvw.mcmaster.com/#5698k7/=yvrc7r.
Dwyer Instrument Series V10 Flotect Switch image via Archive Org Apr. 6, 2012 of http://www.dwyer-inst.com/Product/Flow/FlowSwitches/Paddle/SeriesV10.
Omega website image of Sensoria Archive.Org dated Jun. 21, 2008 of http://www.omega.com/pptst/LV170.html.

* cited by examiner

LIQUID BLOCK PROBE FOR WET GAS

BENEFIT CLAIM

The present application claims the benefit of U.S. Provisional Patent Application Ser. No. 62/049,201 filed Sep. 11, 2014, entitled LIQUID BLOCK PROBE FOR WET GAS, listing as inventor Valmond Joseph St Amant, III.

FIELD OF THE INVENTION

The invention relates to sampling of pressurized process fluids for on-stream and spot sampling of pressurized process fluid such as natural gas or the like, said pressurized process gas having liquid entrained therein, or otherwise referenced as multiphase or "wet". The preferred embodiment of the present invention contemplates a liquid block apparatus integrated into a sample probe that is inserted into the pressurized process to prevent entrained liquids from entering the probe and being extracted for sampling.

BACKGROUND OF THE INVENTION

Natural gas is bought and sold based on its heating value. It is the BTU content that determines the monetary value of a given volume of natural gas. This BTU value is generally expressed in decatherms (one million BTU). In the determination of total heat value of a given volume of gas, a sample of the gas is analyzed and from the composition its heat value per unit volume is calculated. This value is generally expressed in BTU/cu ft. The typical range of transmission quality gas ranges between 1000 and 1100 BTU/cu ft. Production gas, storage facility gas, NGL, and new found Shale Gas can have much higher heating values up to or even exceeding 1500 BTU/cu ft.

There has been a long standing controversy between gas producers and gas transporters regarding entrained liquid typically present in most high BTU/cu ft. gas (rich or "wet" gas). Transporter tariffs require essentially liquid-free gas. Hydrocarbon liquid in the gas being transported causes operational and safety problems. The practice is to separate the liquid before entering a transport (pipe) line.

The API 14.1 standards (Manual of Petroleum Measurement Standards, 2006) scope does not include supercritical fluid (dense phase) or "wet gas" "(a term referenced by the Natural Gas industry as a gas that is at or below its hydrocarbon dew point temperature and/or contains entrained liquid), nor does the GPA 2166 standard (Obtaining Natural Gas Samples for Analysis by Gas Chromatography, 2005). In summary, there is no known standard which defines how to obtain a "representative sample" of a natural gas supply having entrained "liquid" hydrocarbon in any form.

Therefore to fully comply with the current industry standards, there is a need to prevent entrained liquids from entering sample systems. Membrane-tipped probes such as the A+ Corporation Genie Probe (see U.S. Pat. No. 357,304, U.S. Pat. No. 6,701,794, U.S. Pat. No. 6,904,816, U.S. Pat. No. 7,004,041, and U.S. Pat. No. 7,134,318) have been used for many years to shed entrained liquids inside pressurized pipelines. However, they do not have any physical block to stop entrained liquids, should the differential pressure be exceeded, forcing liquids through the coalescing elements, and into the sample system. The differential pressure needed to force liquids through the coalescing elements is a function of the surface tension of the liquid and the construction of the coalescing element. Sometimes man-made liquid chemicals are injected into the process like corrosion inhibitors, amine and carbon dioxide inhibitors as well as chemicals meant to dry the gas like alcohols and glycols. These liquid chemicals may have low surface tensions that could get past some coalescing elements. The liquid chemicals may combine with the sample to lower the surface tension of the sample making it easier for the sample to get past some coalescing elements. Also some coalescing elements may have temperature limitations. Therefore, there is a need for a physical block to stop these liquids from getting into the sample system.

Viewable (transparent) level indicators with floats/valves have been used for many different purposes through the years. For example, McKillop's level indicator with float valve has been used for concrete mixer water tanks (See U.S. Pat. No. 2,725,071) since the 1950s.

Another company, Welker Engineering, utilizes a device similar to the McKillop viewable (transparent) indicator. Welker has a viewable (transparent) liquid protection device (see U.S. Pat. No. 5,579,803) outside a pressurized pipeline to protect gas chromatographs during on-line sampling since 1995. However, these type devices cannot stop aerosols, or mist of liquid. They can only stop large slugs of liquids. The operator is encouraged to view the device to look for mist or aerosols that could get past the device. Then a separate device with a bypass or drain is needed to coalesce the mist or aerosol, and drain it to remove it. A bypass stream or drain is not desirable, since valuable process sample is vented to the atmosphere and/or drained on the ground. In addition, EPA regulations may prohibit such venting and draining of process fluids. Even if the vented gas and drained liquid is sent to a flare, the result must be monitored for safe emissions.

Further, viewable transparent devices such as McKillop's and Welker's are limited in pressure rating due to the transparent material of construction.

More recently, A+ Corporation introduced a liquid valve feature in a Genie Membrane Separator (see U.S. Pat. No. 7,555,964) where a valve is used in conjunction with a phase separation membrane/diaphragm. This method is not designed for conventional probe insertion into pressurized pipelines because the diaphragm diameter used to actuate the valve is large compared to the available opening in the pipeline for probe insertion. The small diameter diaphragms required to fit into the available hole in the pipeline are so small that the analytical flow rate is too limited to be of any practical use. Further, the device is neither transparent nor is the liquid viewable. Nonetheless, this device works well in high pressure applications outside the pipeline, before an analyzer, to protect gas analyzers during on-line sampling and spot sampling, when the safe maximum allowable differential pressure is exceeded so as to force liquids through the phase separating coalescing elements. The diaphragm has no size limitation outside the pipeline since there is no insertion requirement, and therefore no size constraint.

The Genie Membrane Separator device requires a bypass or drain to coalesce any mist or aerosol as a drain for removal. Again, a bypass stream or drain is not desirable since valuable process sample is vented to the atmosphere and/or drained on the ground. In addition, EPA regulations may prohibit such venting and draining of process fluids. Even if the vented gas and drained liquid is sent to a flare, the result must be monitored for safe emissions.

Further, any time liquid is removed from the source and transported into the sample system, the liquid distorts the true composition of the sample. It would be preferable to stop the liquid from ever entering the sample system, to prevent sample distortion and contamination which equates to wrong analysis, and very costly, incorrect monetary exchanges at custody transfer points, for both producers and transporters. In addition, it would also be desirable to have a device that does not need a bypass stream that must be vented to the atmosphere or need a drain that drains the liquids blocked onto the ground.

GENERAL SUMMARY DISCUSSION OF THE INVENTION

The present invention solves the problems discussed above. The device of the present invention is inserted into pressurized pipelines to prevent liquids from entering the sample system. It does not require a bypass stream vented to the atmosphere, nor does it require the draining of liquids onto the ground via drain or the like, or flaring of bypass fluid flow. Rather, the present invention prevents entrained liquids from entering the sample probe, ensuring that either a single gas phase sample is taken, or that no sample is taken at all. This improved technique thus protects the entire sample system from contamination that would require costly downtime for cleaning or replacement. It also prevents sample distortion and incorrect analysis for parties using the current API and GPA sampling standards.

Unlike prior art that requires a transparent and visible viewing port so that liquid levels may be seen, the present invention stops liquid at the source, inside the pipeline. The present invention has walls constructed of stainless steel, to withstand high pressures, thus requiring no pressure reduction before this device.

Unlike prior art, the present invention provides a physical block so that it is not dependent on limitations of surface tension, pressure differentials, temperature or pressure limitations.

One embodiment of the present invention (FIGS. 1-5) provides a liquid block at the tip of a sample probe that is insert-able under pressure into the pressurized pipeline. This liquid block probe may be provided with a coalescing element behind the liquid block, so that the incorporated coalescing element can coalesce entrained mist or very fine aerosol droplets to prevent them from being introduced into the sample system. Then, if a slug of liquid is present in the sample, the liquid block would close and prevent that large slug of liquid from entering the sample system. The liquid block would remain closed until the large quantity of liquid is no longer present, then it would open and allow sample to flow to the coalescing element.

A second embodiment would be a liquid block at the tip of a sample probe that is insert-able under pressure into pressurized pipelines, but without any filter or coalescing element of any type behind the liquid block (FIGS. 6-8). A filter could be placed in front of the liquid block to protect small passageways that may be needed for sizing the flow-to-block ratio of the liquid block. This ratio must be sized correctly so that under normal analytical flow rates in a gas or vapor only single phase sample, the block does not stop the sample. Then the passageways must also be sized so that when liquid slugs are present, the block can move in response to block the sample. The inlet passageways may need to be small to accomplish this. Small passageways have a tendency to get plugged, and may require filtration to prevent that from happening.

A third embodiment would be a fixed probe that requires a meter run section of pipeline to be depressurized for insertion and installation (FIGS. 9-11). This third embodiment could have the other features of the first and second embodiments. The embodiments listed are not intended to be an exhaustive list of applications for the liquid block but only intended to show the need and some of the practical application of the invention. The liquid block may need a manual reset to equalize the pressure upon startup and initial installation into the pressurized pipeline. The liquid block may also need an auto reset or spring-assist return/reset depending on sample pressures and fluid properties. In spot sample applications, it may be desirable that no reset is possible once the liquid block closes so that the technician has no means of allowing liquid to be introduced into the sample cylinder (fool-proof sampling technique). Online or continuous analyzer applications may need an adjustable reset for different pressures or fluids or flows or changing pipeline sample conditions.

The seal necessary to create the block feature of all embodiments could be an O-ring, or a gasket, or any other sealing material. The block could be a lightweight metal or plastic or a plastic coated metal. It could also be ceramic or gems like a sapphire material (FIG. 15). The coalescing element could be a sintered plastic or metal or spun borosilicate glass or membrane material.

Other features could include a sensor that could give the operator an indication that the block is closed. The sensor could be mechanical in nature that would simply be like a go/no go indicator (FIGS. 12-13). It could be spring loaded and mechanically coupled to an indicator at the top of the probe outside the pipeline. The sensor could also be electrical or electromechanical in design. The output of that type of sensor could be sent to a control/information/communication device that would provide that input to the on-line analyzer of spot sample technician. (alarms, telemetry, horns, etc.). The sensor could be powered local to the probe (battery or solar for example) or use the power from the analyzer or the power from the heating tube bundle or enclosure heater.

The sensor could also be something as simple as a flowmeter on the outlet of the probe before the analyzer (FIG. 14). The flowmeter indication of no flow would mean that the liquid block is closed. The flowmeter could have a sensor that sends that information to the on-line analyzer or spot sample technician.

Currently, there is no way to continuously tell if the sample in the pipeline is single phase gas and vapor only, or if significant amounts of liquid are present. Another embodiment of this invention could be mounted to the tip of a probe so that is not only insert-able under pressure, but is also, being on the tip of a probe, it can be cranked up and down at different insertion depths in the pipeline so to get a liquid-free sample. Alternatively, the device could be used to signal the sample owner that liquid is present at different insertion depths inside the pipeline (FIGS. 1,2,6,7,8,12,14).

For example, if the probe were cranked down to touch the opposing pipeline wall and the block shut off, then the sample owner would know that liquid is running along the inside wall of the pipe. Then if the probe was cranked up to the center of the pipe and the liquid block opened, then the sample owner would know that no liquid is present at the center of the pipe. In this embodiment, the probe is used more as a sensor than a sample extraction device. The signal for those conditions could be sent to a local analyzer or control room or to other devices or communication hubs or locations that need that information to make decisions.

BRIEF DESCRIPTION OF DRAWINGS

For a further understanding of the nature and objects of the present invention, reference should be had to the following detailed description, taken in conjunction with the accompanying drawings, in which like parts are given like reference numerals, and wherein.

DETAILED DISCUSSION OF THE INVENTION

Figure 1:
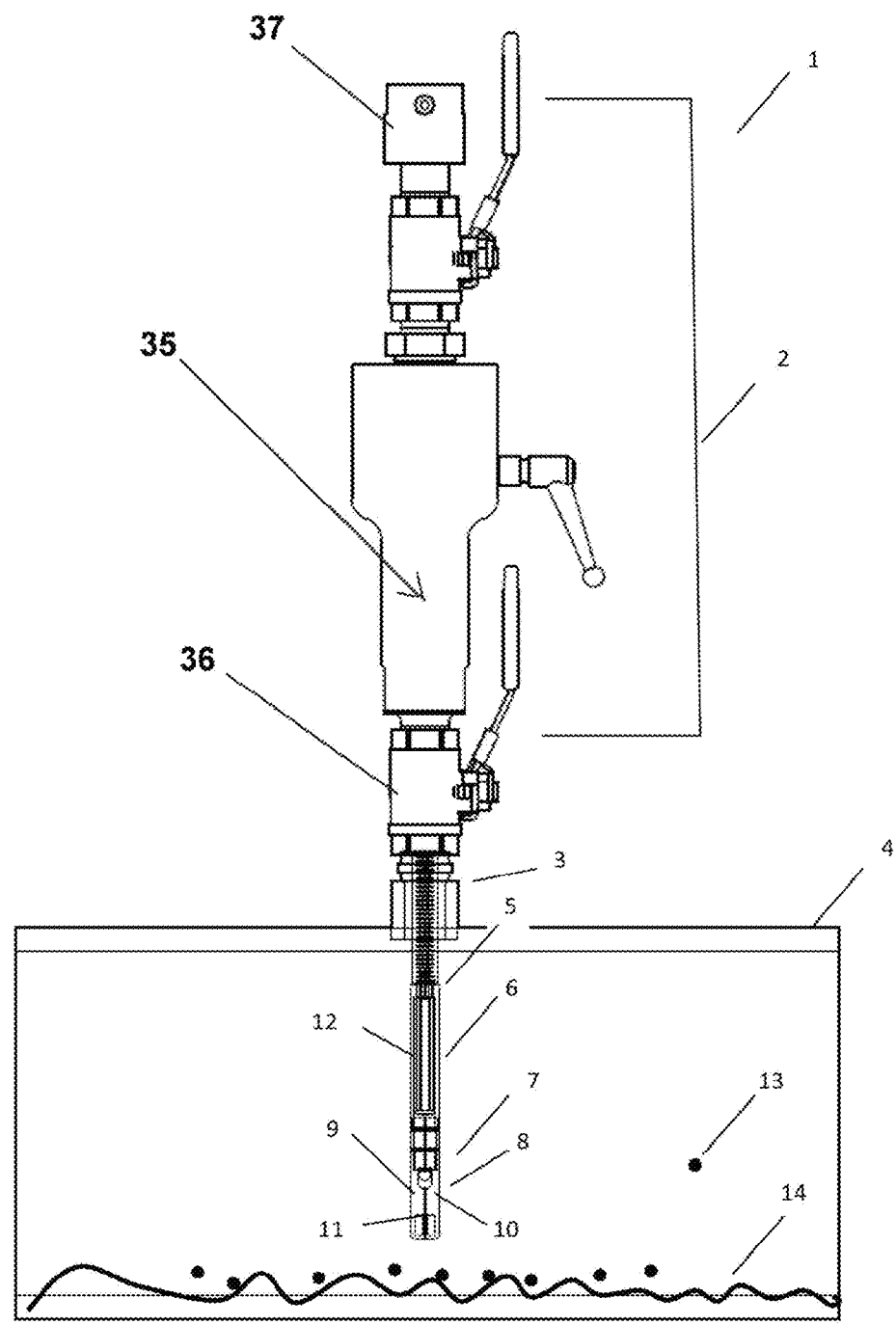
FIG. 1 is a frontal, partially cutaway view of the first embodiment of the present invention, illustrating a liquid block mounted to the tip of the sample probe having a passage 35 formed longitudinally therethrough, the probe facilitating the insertion of the probe tip 5 under pressure into a pressurized pipeline, the present embodiment further illustrating a coalescing element downstream the liquid block, the probe 2 illustrated in the figure being an insertion probe formed to pass through isolation valve 36 into pipeline 4, and is shown having pressure reducer 37 mounted thereto.
Figure 2:
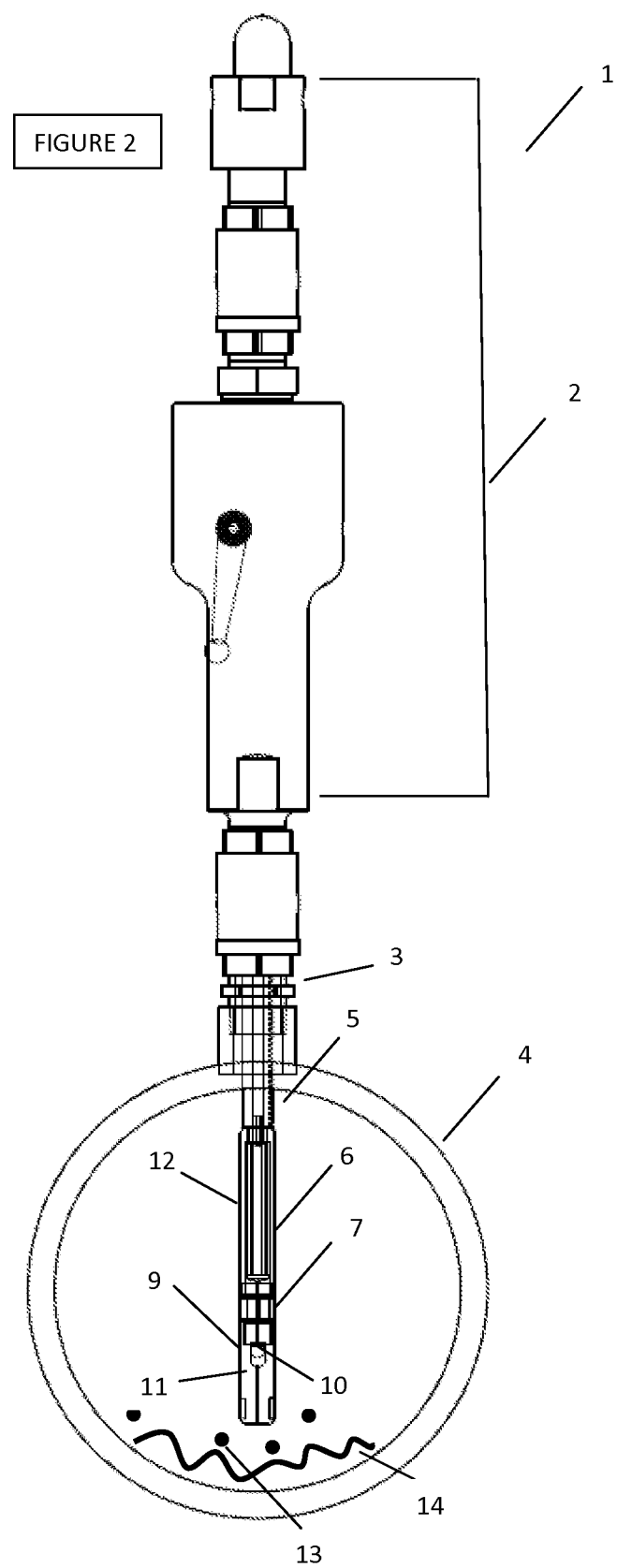
FIG. 2 is an end, partially cutaway view of the invention of FIG. 1.
Figure 3:
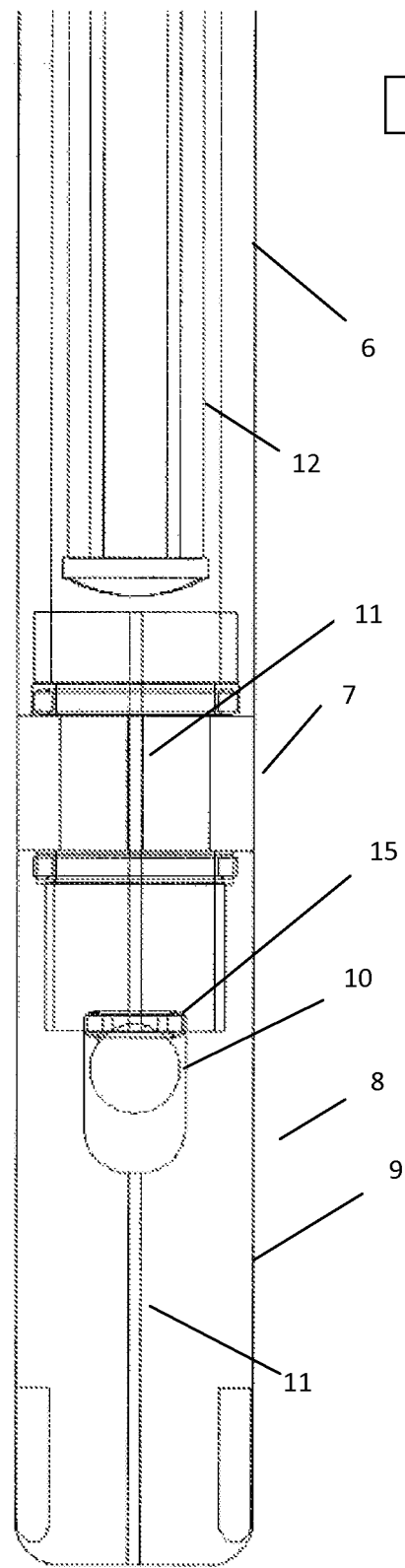
FIG. 3 is a side, cutaway view of the invention of FIG. 1, illustrating a close-up of the probe tip, liquid block, and downstream coalescing element.

The first embodiment 1 of the present invention (FIGS. 1-4) contemplates a liquid block 8 situated in the vicinity of the tip 5 of a sample probe 2 that is insert-able under pressure into the pressurized pipeline 4. The liquid block probe may have a coalescing element 12 behind the liquid block 8 so that the coalescing element 12 can coalesce entrained mist or very fine aerosol droplets 13 that flow past the liquid block to prevent said entrained mist or aerosol droplets 13 from being introduced into the sample system. Further, as desired, a pressure reducer 37 or pressure cut may be provided downstream the coalescing element, via passage 35, for pressure reduction downstream.

As further described herein, the liquid block 8 is configured to close and prevent flow therethrough of a slug of liquid 14 having a predetermined minimal mass, so as to prevent same from entering the sample system. The liquid block would remain closed until the large quantity of liquid is no longer present, then it would open and allow sample to reach the coalescing element 12 once again.

Figure 4:
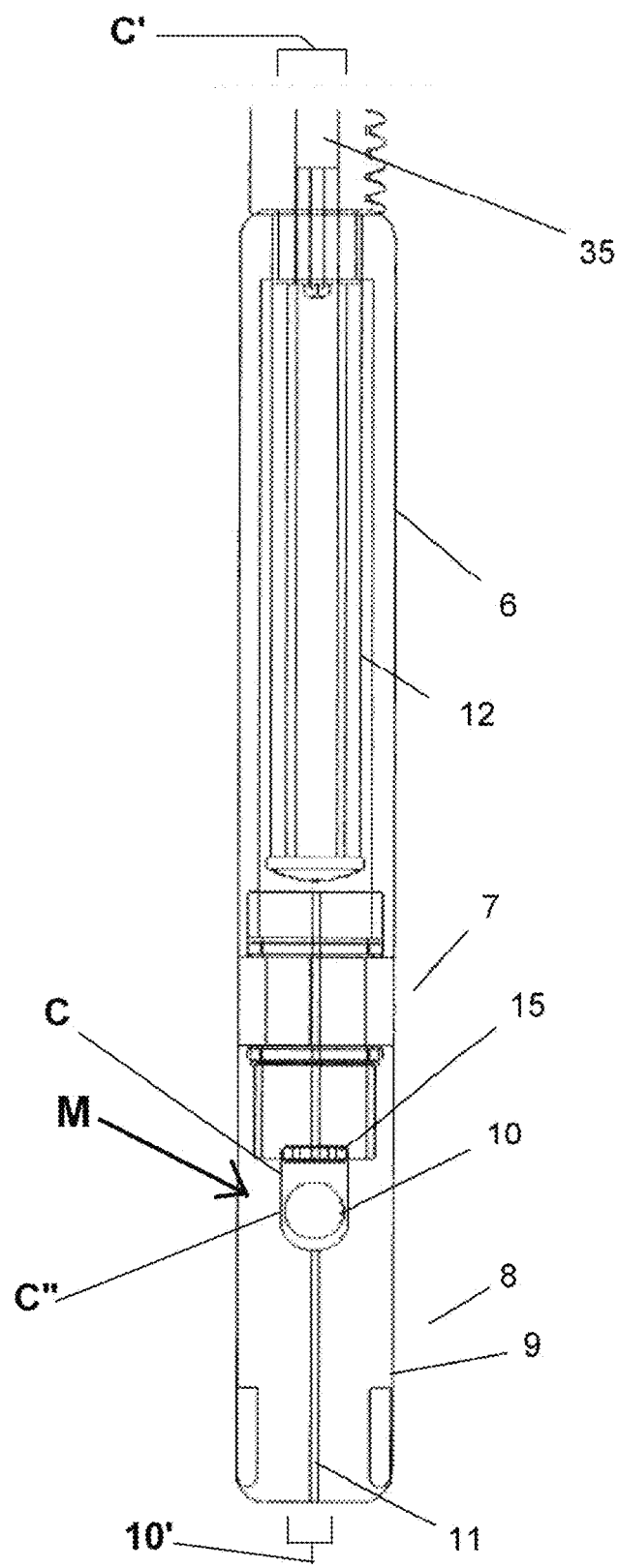
FIG. 4 is a side, cutaway, alternative view of FIG. 3.
Figure 5:
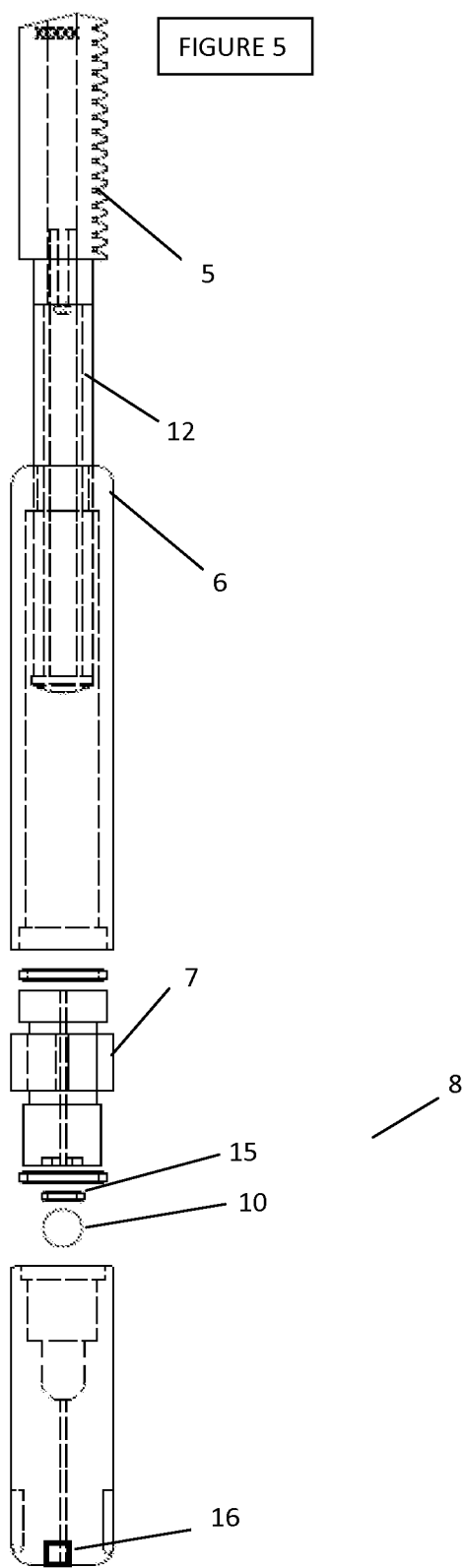
FIG. 5 is a side, exploded, close-up view of the probe tip area of the invention of FIG. 1 illustrating internal configurations in phantom.

An exemplary embodiment of a liquid block installable on the tip 5 or end of a probe that is insertable under pressure is shown comprising a chamber C having a inner diameter (ID) C', said chamber C having situated therein a moveable body M, shown in the form of a mechanical float/ball 10 having an outer diameter (OD) 10' which is preferably less than the inner diameter (ID) C' of chamber C, so as to form a clearance C" therebetween. Said float/ball 10 is situated to freely move about within said chamber C to selectively engage a downstream seal 15 formed of, for example, an O-ring or gasket material. Float/ball 10 is situated within said chamber C in an unattached or unencumbered manner so as to facilitate the repositioning of same upon engagement with a slug of liquid in chamber C, said slug or mass of liquid displacing said float/ball 10 by applying force against said float/ball 10, so as to facilitate repositioning of said float/ball against said seal, thereby blocking further flow of said slug of liquid within the device so as to prevent migration of said liquid mass therethrough. FIG. 4 shows the float/ball 10 within chamber so as to facilitate the normal flow of gas through chamber C uninterrupted, as the gas flows about said float/ball 10 via said clearance C', the gas having insufficient mass to motivate said float/ball 10. Upon the float/ball 10 interacting with the slug of liquid, the float/ball 10 is urged or motivated by the slug of liquid to reposition to sealingly engage seal 15 as long said slug of liquid engages or applies force or bias to said float/ball 10. Upon said slug of liquid disengaging from said float/ball 10 and draining from chamber to said fluid stream, said force or bias is diminished or removed to allow gravity to facilitate the separation of said float/ball from said seal, allowing gas or fluid to flow therethrough.

Figure 15:
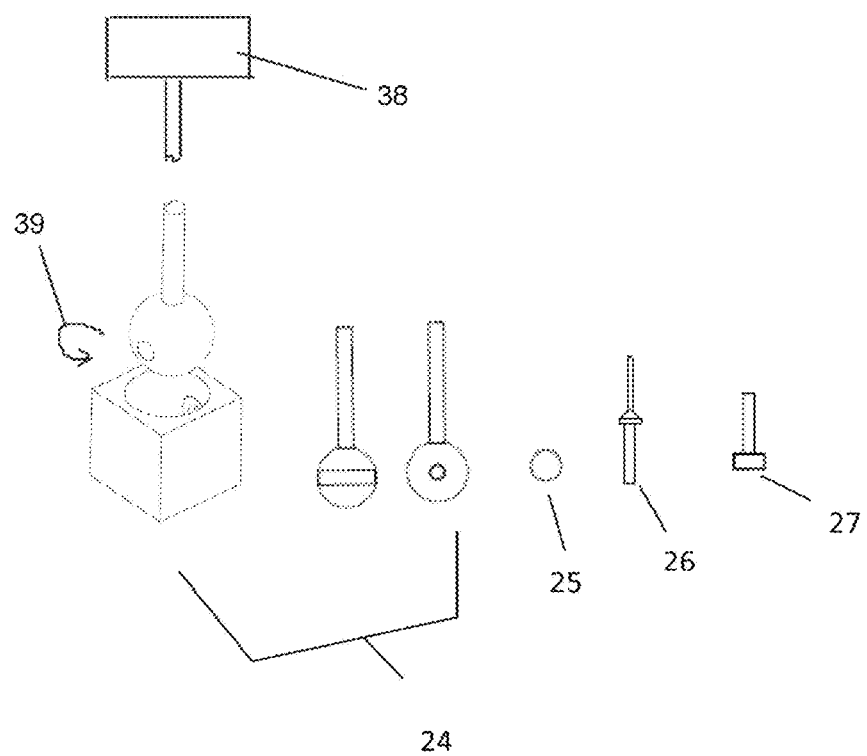
FIG. 15 illustrates an exemplary rotary-type solenoid-actuated valve configured to selectively block the flow from the probe depending upon the pressure condition.

The present illustration is not meant to limit the block design to be a ball/O-ring design, since the block could be made from many different shape floats or even a rotating ball/wiper seal arrangement or a sliding plate arrangement, actuated door, shutter or the like, actuated by a sensor (FIG. 15). The diameter and length of the passageways 11 as well as the material of construction and area/size of the block may be application dependent (i.e. may depend on process fluid, analytical flow rate thru probe, the properties of the type of liquid entrained, etc.). For example, small diameter long passageways with certain fluid properties may work well with certain block designs.

Figure 6:
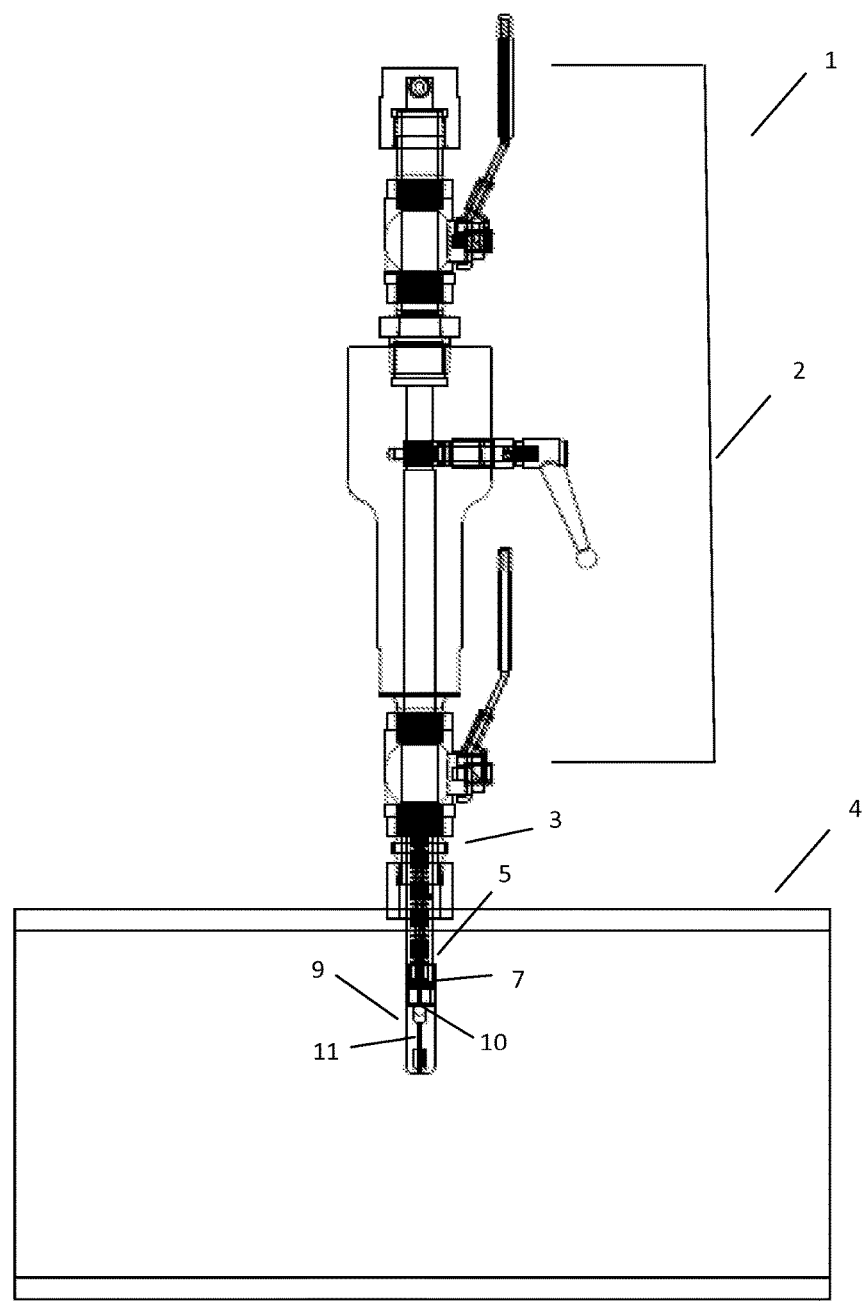
FIG. 6 is a frontal, partially cutaway view of a second embodiment of the present invention, illustrating a liquid block mounted to the tip of the sample probe inserted under pressure in pressurized pipeline, but without the coalescing element of the invention of FIG. 1.
Figure 7:
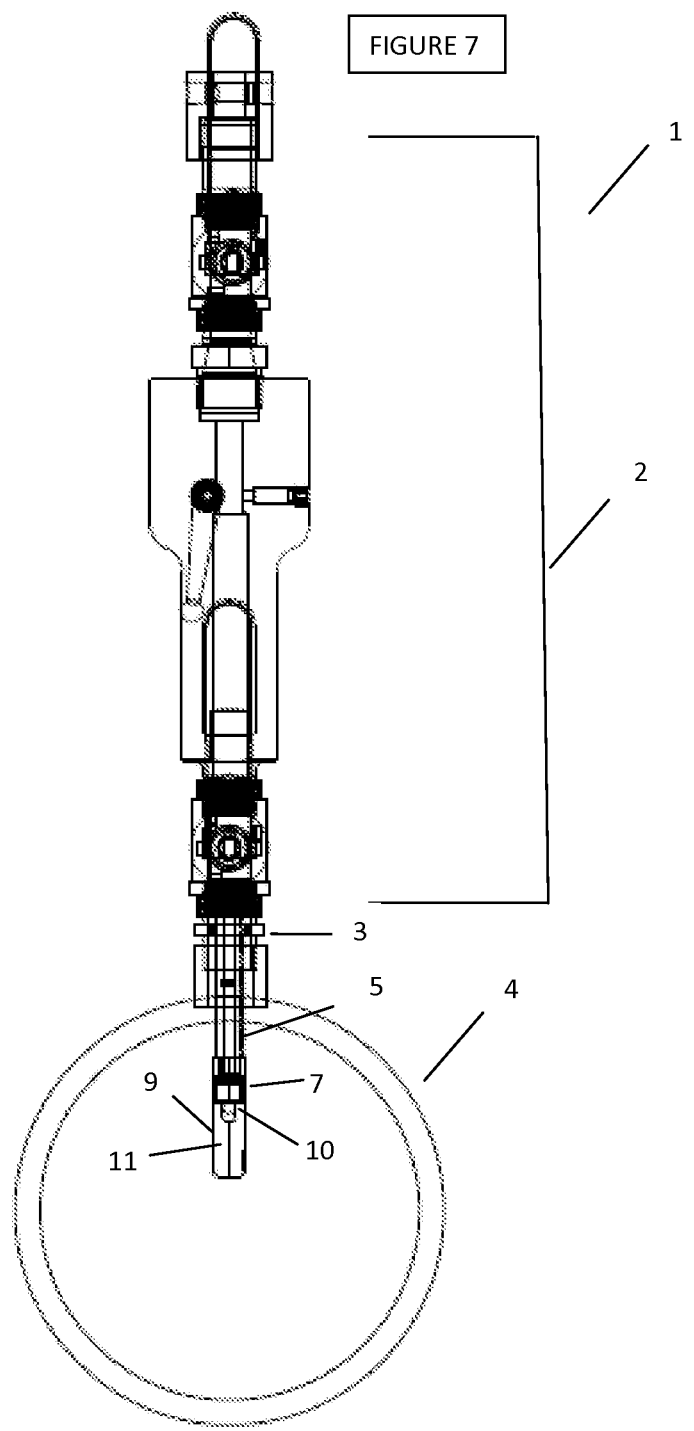
FIG. 7 is an end, partially cutaway view of the invention of FIG. 6.
Figure 8:
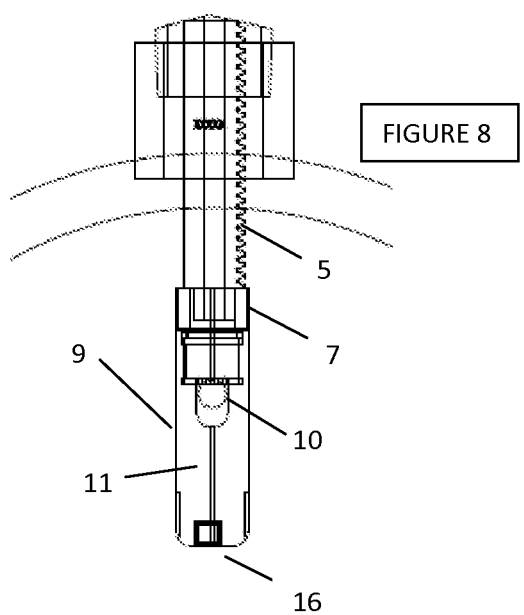
FIG. 8 is an end, partially cutaway, close-up view of the invention of FIG. 6.

A second embodiment contemplates a liquid block at the tip of a sample probe that is insert-able under pressure into pressurized pipelines, but without any filter or coalescing element of any type behind the liquid block (FIGS. 6-8). A particulate filter such as sintered metal or a screen 16 could be placed in front of the liquid block to protect small passageways 11 that may be needed for sizing the flow to block ratio of the liquid block. This ratio must be sized correctly so that under normal analytical flow rates in a gas or vapor single phase sample, the block does not stop the sample. The passageways must also be sized so that when liquid slugs are present, the block can move in response to block the sample. The inlet passageways may need to be relatively small to accomplish this. Small passageways may have a tendency to get plugged, so filtration may be required to prevent this from happening. In this second embodiment, a pressure reducer or pressure cut device may be provided downstream the liquid block to reduce pressure downstream therefrom.

Figure 9:
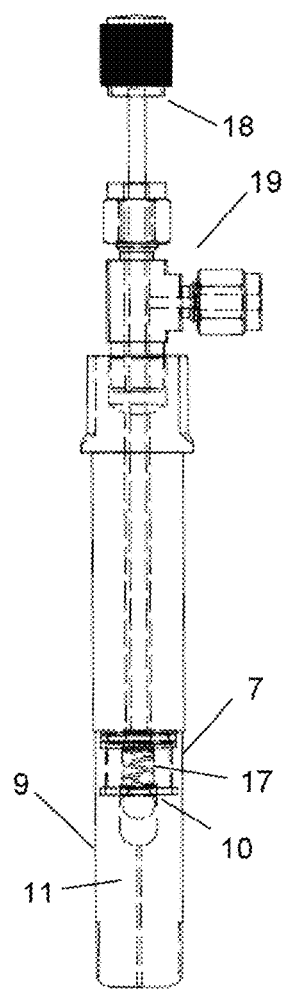
FIG. 9 is a side, partially cutaway view of a fixed probe embodiment of the present invention having a liquid block provided therein near the tip.
Figure 10:
FIG. 10 is a side, partially cutaway view of the invention of FIG. 9, but without the external conduit and reset feature shown.
Figure 11:
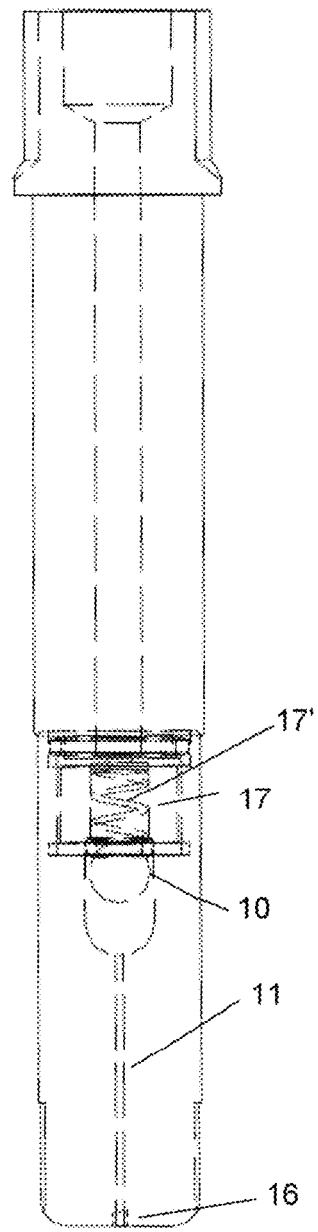
FIG. 11 is a close-up view of FIG. 10, providing in large details of the liquid block mechanism.
Figure 12A:
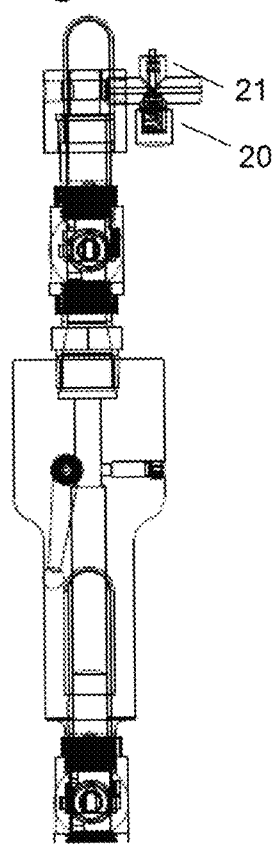
FIG. 12A illustrates a side, partially cutaway view of the invention, particularly illustrating the No-Go device indicating a depressurized condition, with the indicator in the extended position from the housing.
Figure 12B:
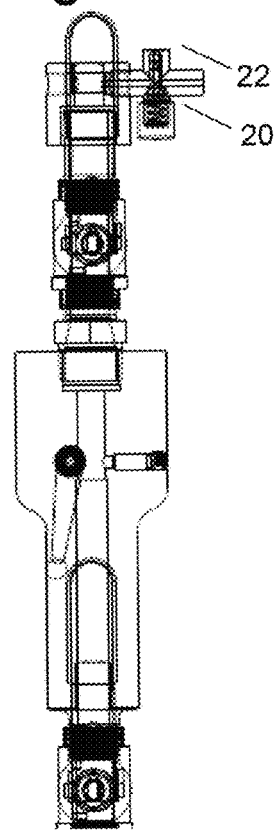
FIG. 12B illustrates the invention of FIG. 12 a, but with the No-Go device indicating a pressurized condition, with the indicator retracted into the housing.
Figure 13A:
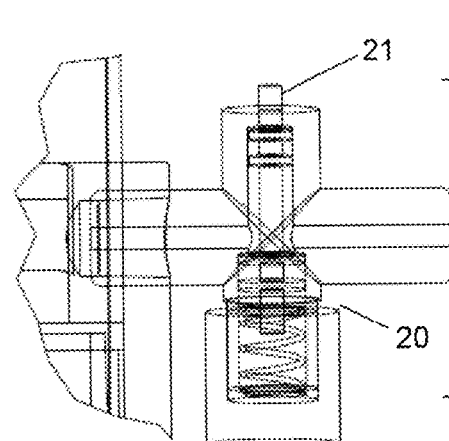
FIG. 13A is a side, partially cutaway, view of the invention of FIG. 12A.
Figure 13B:
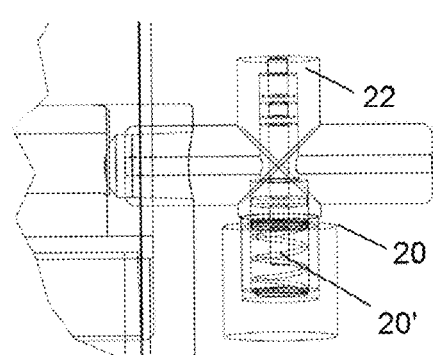
FIG. 13B is a side, partially cutaway, view of the invention of FIG. 12B.

A third embodiment contemplates a fixed probe requiring, for example, a meter run section of pipeline to be depressurized for insertion and installation (FIGS. 9-11). This third embodiment could have the other features of the first and second embodiments. The embodiments listed are not intended to be an exhaustive list of applications for the liquid block but only intended to show the need and some of the practical applications of the invention. The liquid block may need a manual reset 18 to equalize the pressure upon start-up and initial installation into the pressurized pipeline.

The liquid block may also need an auto reset or spring-assist return reset 17 utilizing spring 17' to provide spring bias, whether it is required depending on sample pressures and fluid properties. Also, the "reset pressure" of the liquid block may require the seal area to be adjusted depending on process pressure and passageway size and block and seal construction. Once the block has been engaged and sealed, the surface area of the seal may need to be adjusted relative to the process conditions as well as possibly requiring a biased spring assist.

Other embodiments could include a sensor 40 that could give the operator an indication that the block B is closed. The sensor could be mechanical in nature, for example, a go/no go indicator (FIGS. 12A-13B). The sensor could be in the form of a spring 20' loaded or biased indicator and mechanically coupled at the top of the probe outside the pipeline. This type of sensor as described could act as an indicator and would be preferred in hazardous or electrically classified areas that do not allow electrical or electronic devices. The sensor/indicator as described is pressure balanced to remain inside or in the "down" position 22 relative to its housing when the liquid block is open and the housing is pressurized but then when the block closes and the housing depressurizes, then the spring pushes the indicator to pop up 21 or out of the housing (in the present case, for an external indicator assembly 20). The sensor could also be electrical or electromechanical in design.

Figure 18:
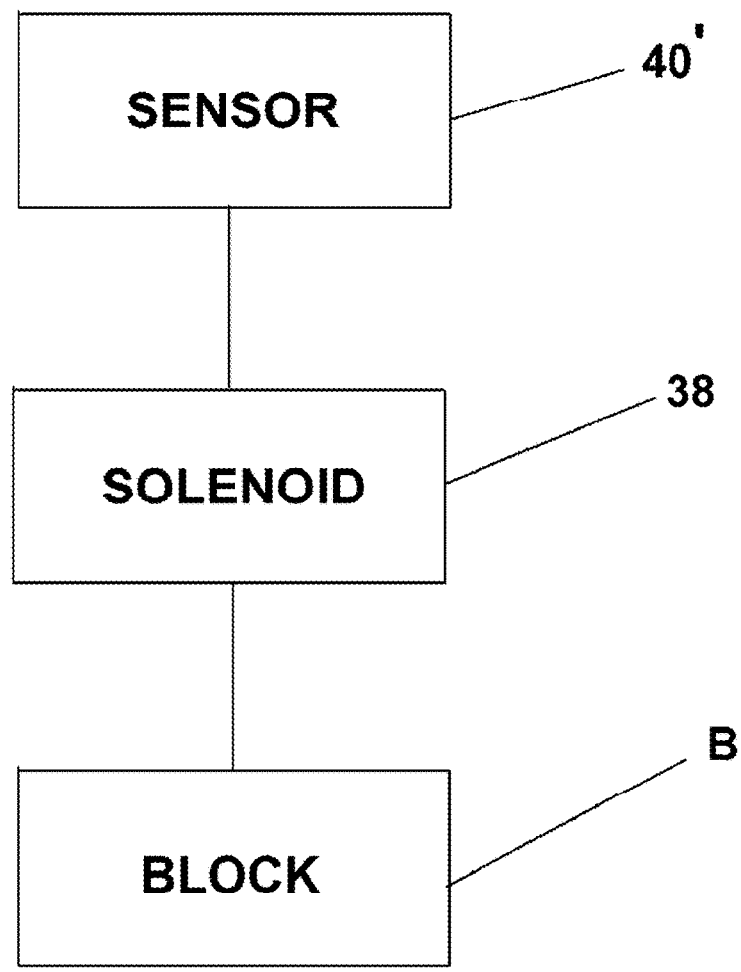
FIG. 18 is a block diagram illustrating the block B of the present invention actuated by a solenoid 38 or actuator via a sensor 40'.

The output of such a sensor 40' could be used to operate a an electromagnetic controller such as a solenoid 38 or actuator that rotates 39 a rotary style block 24, or otherwise actuates one of various styles of a block B to selectively block flow (see FIG. 15, alternative block configurations are shown in items 25-27; see also FIG. 18). The output of the sensor could, for example, also be used to pull a magnetic ball 25 closed by an electromagnetic device such as a surface-contact, DC-Powered Electromagnet or the like, for example, similar to McMaster-Carr D.C. Powered Electromagnet model 5698K7, one shown at www.mcmaster.com, or sensor such as a FLOTECT brand Mini-Size Flow Switch, Series V10, as provided by Dwyer Instruments, www.dwyer-inst.com, or communicate a telemetry signal if flow in pipeline is stopped and the sample no longer needs to be analyzed.

Sensor 40' could further comprise a liquid sensor such as, for example, the optical Liquid-Level Sensor LV170 Series by OMEGA at http://www.omega.com/pptst/LV170.html might be used to actuate the liquid block closed and the output of that type of sensor could also be sent to a control/information/communication device (Alarms, telemetry, horns, etc.) that would provide that input to the on-line analyzer of spot sample technician. This type of sensor may be beneficial to use in remote locations where technicians may not always be on site. This type of sensor could also be used to actuate a rotary or slide type block mechanism. The sensor could be powered local to the probe (battery or solar for example) or it could use the power from the analyzer or the power from the heating tube bundle or enclosure heater.

Figure 14:
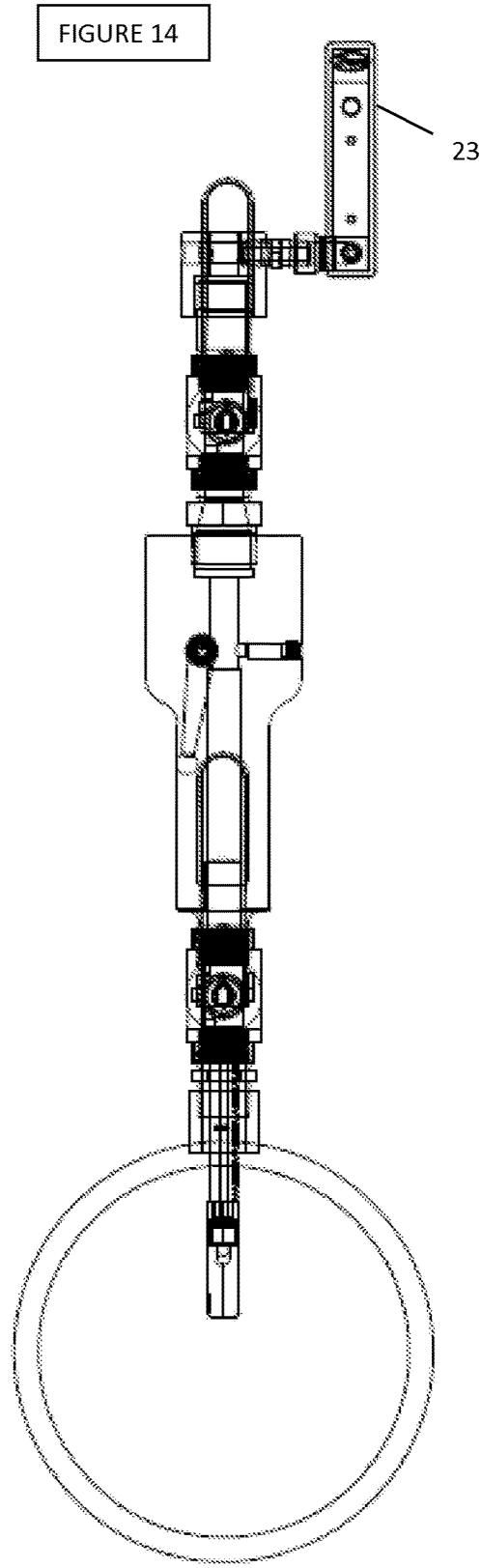
FIG. 14 is a side, partially cutaway view of the invention of FIG. 6, further including a flow meter at the outlet of the probe, for example, before the analyzer.

The sensor could also be something as simple as a flowmeter 23 on the outlet of the probe before the analyzer (FIG. 14). The flowmeter indication of no flow would mean that the liquid block is closed. The flowmeter could have a sensor (such as the above referenced FLOTECT Series V10 Switch) that sends that information to the on-line analyzer or spot sample technician.

The above references to the Exemplary FLOTECT, OMEGA products, or electromagnet device, are not meant to be limiting in any way but are only used to illustrate examples of typical sensors/devices available.

Figure 16:
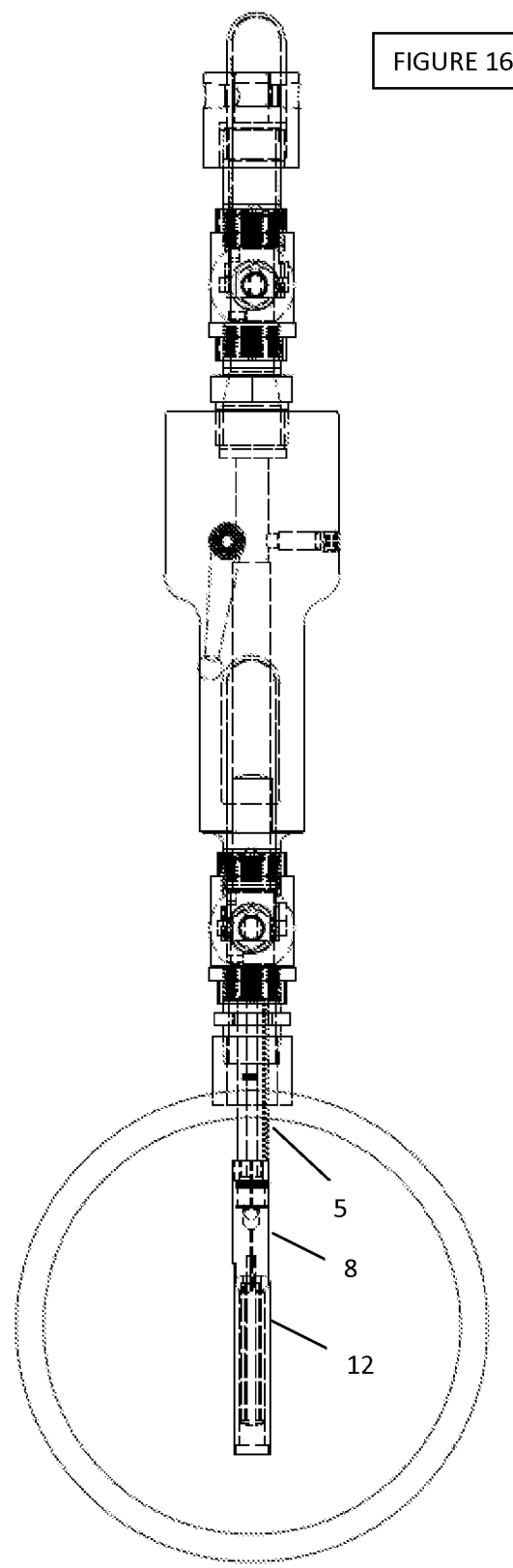
FIG. 16 is a frontal, partially cutaway view of another embodiment of the present invention, illustrating a liquid lock mounted to the tip of the sample probe inserted under pressure in pressurized pipeline, but with the coalescing element upstream of the liquid block, as opposed to downstream the liquid block, as illustrated in FIG. 1.

In spot sample applications it may be desirable that no reset is possible (FIG. 16) once the liquid block closes so that the technician has no means of allowing liquid to be introduced into the sample cylinder (fool-proof sampling technique). In those cases, the coalescing filter is in front of the liquid block (FIG. 16). Online or continuous analyzer applications may need an adjustable reset (FIG. 9) for different pressures or fluids or flows or changing pipeline sample conditions.

Figure 17:
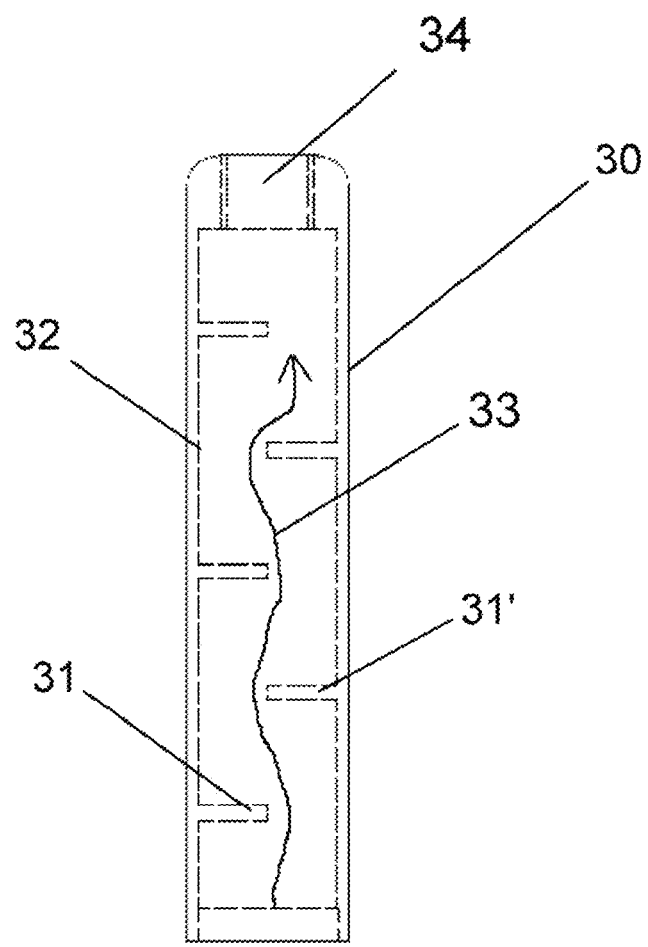
FIG. 17 is a side, cutaway view of an alternative liquid block illustrating a flow enclosure 30 having an inner wall 32 forming a barrier provided by a series of interior shelves forming barriers to dissipate liquid flow in the fluid stream, comprising first 31 and second 31' opposing barriers, the barriers spaced and to allow the passage 33 of gas therebetween to outflow passage 34.

Another type of liquid block is envisioned that is a barrier formed by interior shelves that block the liquid differently than a shut off liquid block (FIG. 17). Since the liquid block is on a probe tip inside the pressurized pipeline, the actual velocity is lower than outside the pipeline at lower pressures. In some cases that do not have extreme liquid problems, inertial separation may block the liquid.

ELEMENT LISTING

1 First Embodiment
2 probe
3 Process Connection and isolation valve
4 pipeline
5 tip
6 shroud/connection to probe tip
7 tip assembly joint
8 liquid block
9 Liquid block housing
10 float/ball
11 passageways
12 coalescing element
13 droplets 14 slug of liquid
15 seal
16 screen
17 spring-assisted return/reset, 17' spring
18 manual reset plunger
19 manual reset outlet connection
20 external indicator assembly, 20' spring
21 external indicator in the "up" position (pops out of housing)
22 external indicator in the "down" position (inside housing)
23 flowmeter
24 rotary style block
25-27 alternative block configurations
30 flow enclosure
31,31' first, second barriers
32 inner wall
33 passage
34 outflow passage
35 passage
36 isolation valve
37 pressure reducer
38 solenoid or actuator
39 rotates
40, 40' sensor
B block
M Moveable body The invention embodiments herein described are done so in detail for exemplary purposes only, and may be subject to many different variations in design, structure, application and operation methodology. Thus, the detailed disclosures therein should be interpreted in an illustrative, exemplary manner, and not in a limited sense.

I claim:

1. A device for sampling a fluid in a fluid stream, comprising:
    a liquid block in fluid communication with a probe tip on a probe having a passage longitudinally therethrough, said probe tip situated in and formed to receive fluid from said fluid stream;
    said liquid block comprising a moveable body freely situated within a chamber in an unattached or unencumbered manner, said chamber having a seal downstream said moveable body, said moveable body formed to be repositionable to selectively engage said seal by a mass of liquid flowing therein via the application of force from said mass of liquid against said moveable body;
    a coalescing element downstream said liquid block, said coalescing element having a passage situated downstream therefrom;
    whereby, upon said mass of liquid flowing into said chamber and engaging said moveable body, a force is applied to said moveable body by said mass of liquid so as to reposition said moveable body to engage said seal to block the flow of said mass of liquid therethrough and interrupt flow to said coalescing element; and
    whereby, upon said mass of liquid receding from said chamber, said force is diminished or no longer applied to said moveable body by said mass of liquid, so as to facilitate said moveable body disengaging from said seal, and allow the flow of fluid therethrough to said coalescing element.

2. The device of claim 1, wherein there is provided a coalescing element situated upstream of said liquid block.

3. The device of claim 1, wherein said probe comprises an insertion probe.

4. The device of claim 3, wherein said fluid stream is situated in a pipeline, and wherein said probe is fixed to said pipeline.

5. The device of claim 1, wherein there is provided a particulate filter situated upstream of said liquid block.

6. The device of claim 5, wherein said particulate filter is formed to allow the flow of fluid therethrough, while resisting the flow of particulates therethrough.

7. The device of claim 6, wherein said particulate filter comprises sintered metal.

8. The device of claim 6, wherein said particulate filter comprises a screen.

9. The device of claim 1, wherein said moveable body is formed to receive force from said mass of liquid so as to position said moveable body against said seal for only as long as said force is applied thereto.

10. The device of claim 9, wherein said moveable body has an outer diameter, said chamber has an inner diameter, said outer diameter of said moveable body being less than said inner diameter of said chamber so as to provide a clearance therebetween, to facilitate the flow of gas therethrough.

11. The device of claim 10, wherein said moveable body comprises a float.

12. The device of claim 11, wherein said coalescing element comprises a gas permeable membrane.

13. The device of claim 12, wherein there is provided a passage formed downstream said coalescing element, said coalescing element formed to allow the flow of gas therethrough, while blocking the flow of entrained liquid therethrough.

14. The device of claim 13, wherein there is further provided a pressure reducer downstream said coalescing element.

15. The device of claim 9, wherein said seal comprises gasket material.

16. The device of claim 15, wherein said moveable body is mechanically actuated.

17. The device of claim 9, wherein said seal comprises an o-ring.

18. The device of claim 1, wherein said liquid block is situated in said probe tip.

19. The device of claim 18, wherein said moveable body is positioned to engage said seal by said mass of liquid, so as to selectively block the flow of liquid therethrough.

20. The device of claim 19, wherein said coalescing element is formed to allow the flow of gas therethrough, while blocking the flow of entrained liquid therethrough.

21. The device of claim 20, wherein said coalescing element comprises a gas permeable membrane.

22. The device of claim 18, wherein said fluid stream is situated in a pipeline, wherein said probe comprises an insertion probe selectively insertable in said pipeline so as to retrieve a sample of gas therefrom.

23. The device of claim 22, wherein said probe is formed for insertion into said pipeline via an isolation valve.

24. The device of claim 18, wherein there is further provided a pressure reducer downstream said liquid block.

25. An apparatus for sampling a fluid in a fluid stream, comprising:
    a liquid block situated in a probe, said probe having a longitudinal passage formed therethrough and a probe tip situated in said fluid stream, said liquid block having an opening to receive fluid from said fluid stream via said probe tip, said liquid block formed to selectively block passage of fluid therethrough to a coalescing element, said coalescing element formed to allow the flow of gas therethrough, while blocking the flow of entrained liquid therethrough, said coalescing element having a passage situated downstream therefrom;

said liquid block comprising a moveable body within a chamber, said chamber having a seal downstream said liquid block;

a solenoid or actuator engaging said moveable body to selectively reposition said moveable body within said chamber;

said moveable body comprising a rotary or slide mechanism;

a sensor positioned to actuate said solenoid or actuator upon the detection of liquid upstream said moveable body;

whereby, upon said sensor detecting a mass of liquid upstream said moveable body, said solenoid or actuator is configured to reposition said moveable body to engage said seal, so as to prevent the flow of said mass of liquid therethrough and interrupt fluid flow to said coalescing element; and whereby, upon said mass of liquid no longer being detected by said sensor, said solenoid or actuator repositions said moveable body away from said seal, allowing the flow of fluid therethrough to said coalescing element.

26. The device of claim 25, wherein there said liquid block further comprises a reset for unseating said moveable body from said seal.

27. The device of claim 26, wherein said reset is manually actuated.

28. The device of claim 27, wherein said reset is automatic.

29. The device of claim 28, wherein said reset is electronically actuated.

30. The device of claim 29, wherein said reset is mechanically actuated.

31. The device of claim 26, wherein said liquid block is configured to provide an indication of flow condition.

32. The device of claim 31, wherein said signal is provided via visual indication.

33. The device of claim 32, wherein said visual indication comprises an external indicator formed move to an up position so as to be visually discernable.

34. The device of claim 31, wherein said signal is provided via electronic signal.

35. The device of claim 34, wherein said sensor is formed to transmit telemetry upon predetermined operational criteria.

36. The device of claim 31, wherein there is further provided a flow meter formed to control said signal depending upon a change in flow condition.

37. The device of claim 31, wherein there is further provided a sensor formed to control said signal upon to a change in pressure.

38. The device of claim 37, wherein said sensor is spring biased.

39. The device of claim 25, wherein said moveable body is electromagnetically actuated.

40. The device of claim 39, wherein there is further provided a liquid sensor formed to control an electromagnetic controller formed to selectively position said moveable body at or away from said seal.

41. The device of claim 39, wherein there is further provided a spring bias formed control the position of said moveable body at or away from said seal.

* * * * *